US007250601B2

(12) United States Patent
Kaji et al.

(10) Patent No.: US 7,250,601 B2
(45) Date of Patent: *Jul. 31, 2007

(54) ENERGY SPECTRUM MEASURING APPARATUS, ELECTRON ENERGY LOSS SPECTROMETER, ELECTRON MICROSCOPE PROVIDED THEREWITH, AND ELECTRON ENERGY LOSS SPECTRUM MEASURING METHOD

(75) Inventors: Kazutoshi Kaji, Hitachi (JP); Takashi Aoyama, Naka (JP); Shunroku Taya, Mito (JP); Shigeto Isakozawa, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/372,057

(22) Filed: Mar. 10, 2006

(65) Prior Publication Data

US 2006/0163479 A1    Jul. 27, 2006

Related U.S. Application Data

(63) Continuation of application No. 10/778,327, filed on Feb. 17, 2004, now Pat. No. 7,067,805.

(30) Foreign Application Priority Data

Nov. 21, 2000 (JP) ............................. 2000-359475
Nov. 12, 2001 (JP) ............................. 2001-346019

(51) Int. Cl.
  *H01J 47/00* (2006.01)
(52) U.S. Cl. ....................................... 250/305; 250/311
(58) Field of Classification Search ................ 250/305, 250/306, 307, 311, 397, 398
See application file for complete search history.

(56) References Cited

U.S. PATENT DOCUMENTS

| 5,004,918 | A |   | 4/1991 | Tsuno et al. |   |
|---|---|---|---|---|---|
| 5,590,168 | A |   | 12/1996 | Iketaki |   |
| 5,798,524 | A | * | 8/1998 | Kundmann et al. | 250/305 |
| 6,184,524 | B1 | * | 2/2001 | Brink et al. | 250/305 |

(Continued)

FOREIGN PATENT DOCUMENTS

JP    10-213538    8/1998

(Continued)

OTHER PUBLICATIONS

A. Bleloch et al., "Canceling Energy Drift in a PEELS Spectrometer," Inst. Phys. Conf. Ser. No. 161: Section 5; IOP Publishing, No. 161, pp. 195-198.

(Continued)

*Primary Examiner*—Kiet T. Nguyen
(74) *Attorney, Agent, or Firm*—Dickstein Shapiro LLP

(57) ABSTRACT

An electron beam detector detects a peak of a spectrum, and when a peak position is deviated from a reference position on the electron beam detector, a controller for controlling an electron beam position on the electron beam detector is used to correct a deviation. An electron energy loss spectrum is measured while controlling correction a deviation between an electron beam position on a specimen, and a peak position of the spectrum, and a spectrum measuring with the electron beam detector.

8 Claims, 10 Drawing Sheets

U.S. PATENT DOCUMENTS 6,703,613 B2  3/2004  Kaji et al.
7,067,805 B2 *  6/2006  Kajl et al. .................. 250/305

FOREIGN PATENT DOCUMENTS

| JP | 11-067138 | 3/1999 |
|---|---|---|
| JP | 2000-113854 | 4/2000 |
| JP | 2000-348670 | 12/2000 |
| WO | WO 00/41206 | 7/2000 |

OTHER PUBLICATIONS

K. Yoshida et al., "A Partially Metalbacked YAG Scintillator for Parallel Detector in EELS," Journal of Electron Microscopy, Japanese Society for Electron Microscopy, Tokyo, JP, vol. 39, No. 4, Aug. 1, 1990, pp. 273-274.

* cited by examiner

| ELEMENT NUMBER | ELEMENT SYMBOL | INNER SHELL | BOND ENERGY (eV) | DISPERSION (eV/ch) |
|---|---|---|---|---|
| 7 | N | K | 400 | 0.3 |
| 8 | O | K | 532 | 0.3 |

ENERGY SPECTRUM MEASURING APPARATUS, ELECTRON ENERGY LOSS SPECTROMETER, ELECTRON MICROSCOPE PROVIDED THEREWITH, AND ELECTRON ENERGY LOSS SPECTRUM MEASURING METHOD

CROSS REFERENCE TO RELATED APPLICATIONS

The present application is a continuation of U.S. application Ser. No. 10/778,327, filed Feb. 17, 2004, now U.S. Pat. No. 7,067,805, the disclosure of which is herewith incorporated by reference in its entirety.

BACKGROUND OF THE INVENTION

The present invention relates to an electron energy loss spectrum measuring apparatus, a transmission electron microscope or a scanning transmission electron microscope, and an electron energy loss spectrum measuring method.

As semiconductor devices and magnetic head elements become small and microscopic, the elements has a structure where thin films of several nm (nanometer) are laminated in an area of about submicron. Since the structure, the element distribution, the crystal structure, and the chemical bonding state of the micro area largely affect characteristics of the semiconductor elements and the magnetic head elements, it is important to analyze the micro area.

Methods for observing the micro area include a scanning electron microscope (SEM), a transmission electron microscope (TEM), and a scanning transmission electron microscope (STEM). The TEM and the STEM have a spatial resolution at nanometer level. The TEM is an apparatus which irradiates an electron beam almost parallel to a specimen, and magnifies the transmitted electron beam with a lens or the like. On the other hand, the STEM converges an electron beam into a micro area, measures the transmitted electron beam while scanning the electron beam in two dimensions on a specimen, and obtains a 2D image.

An energy loss specific to an element (electron structure) is generated by an interaction with the elements constituting a specimen when an electron beam transmits through the specimen in the TEM and the STEM. Electron energy loss spectroscopy (EELS) uses an electron spectrometer to apply an energy analysis to electrons which have transmitted through the specimen, and is an analyzing method which can analyze elements in the specimen. A difference in chemical bonding state of identical elements especially reflects the electron structure of the element, and is appears as an energy shift at a level of a few eV. As a conventional analyzing apparatus, the TEM or the STEM combined with an electron energy loss spectrometer (EELS) of parallel detection type is widely used.

An electron beam transmits through a specimen, passes through an objective lens, a projection lens, and an incident aperture, and enters into the EELS in the STEM. The EELS has such a structure that a magnetic sector in a fan shape serves as an electron spectrometer, a quadrupole electromagnetic lens and a hexapole electromagnetic lens are provided front and behind of it, and a parallel type electron beam detector is provided most downstream. The quadrupole electromagnetic lens is used for adjusting a focus of an electron energy loss spectrum, and magnifying the electron energy loss spectrum. The hexapole electromagnetic lens is used to reduce an aberration of the electron energy loss spectrum projected on the electron beam detector. The electron energy loss spectrum magnified by the quadrupole electromagnetic lens is projected on the electron beam detector, and the electron energy loss spectrum spanning a wide range is measured.

The electron beam detector comprises a scintillator receiving an electron beam and emitting fluorescence, and an element comprising multiple pixels for receiving the fluorescence. Alternately, it is a detector comprising multiple pixels for receiving an electron beam. The electron energy loss spectrum is measured based on the incident fluorescence or electron beam intensity.

Prior art relating to the structure of the EELS includes U.S. Pat. No. 4,743,756, Japanese application patent laid-open publication No. Hei 07-21966, Japanese application patent laid-open publication No. Hei 07-21967, and Japanese application patent laid-open publication No. Hei 07-29544.

SUMMARY OF THE INVENTION

A user has to repeat an operation comprising (1) specifying a location to be measured, (2) specifying an element or an energy range to be measured, and (3) using an EELS to measure an electron energy loss spectrum at points to be measured for a conventional analyzing apparatus constituted by combining an STEM with an EELS. Alternately, a location to be measured is specified before hand, and the location is stored in a controller for controlling electron beam scan, and conducts operations (2) and (3) described above. There used to be a problem that a pixel position changes when a trajectory of the electron beam changes because of an effect of an external electromagnetic field, thereby degrading energy precision and accuracy of the electron energy loss spectrum.

The degradation of the energy precision and accuracy of the electron energy loss spectrum causes the following problems when the electron energy loss spectrum at a specific location or multiple locations is measured on a specimen as described above.

(A) FIG. 3(b) shows an example where the spectrum precision degrades when an electron energy loss spectrum is measured at a specific position on a specimen. For example, when an electron energy loss spectrum caused by an inner shell electron excitation of oxygen is measured, the measurement takes one second, and a pixel position for coming into the electron beam detector deviates from a reference pixel position (dotted line) because of an effect from an external electromagnetic field generated in this period in the figure. A spectrum indicated in (i) of FIG. 3(b) is detected for 0.5 second from the beginning of the measuring. The energy shifts because of the effect of the external magnetic field as indicated in (ii) of FIG. 3(b) at 0.5 second. In this case, a spectrum after measuring for one second becomes an electron energy loss spectrum shown in (iii) of FIG. 3(b). As the result, a peak shape of oxygen is wide, and a peak position shifts.

(B) FIG. 4(c) shows an example where the spectrum accuracy degrades when the electron energy loss spectrum is measured at multiple locations on a specimen. For example, a specimen has a structure of laminating a material A (constituting element: A), a material with an unknown constituting element (constituting element is assumed to be B), and material and material C (constituting element C), and the individual materials are measured in a sequence of the material A, the material B, and the material C as shown in FIG. 4(a). The materials A, B, and C respectively present peaks at energy positions (a), (b), and (c) indicated in dotted line on the electron energy loss spectrum in FIGS. 4(b) and (c) if there is no effect from an external electromagnetic field or the like. Even if a component element is an unknown material B, it is determined that the material is composed with the element B according to the energy peak position. When a measurement is conducted sequentially from the material A, if the energy shifted because of an external electromagnetic field while an electron beam is maintained on the material B during measuring, the spectrum of the material B shifts as shown in FIG. 4(c). When the element from the material B is identified based on spectra at individual measured points, there is a problem that a false result is obtained.

Prior art for solving this problem includes U.S. Pat. No. 5,798,524 and Japanese application patent laid-open publication No. 2000-113854. However, they cannot solve the problem described in (B).

Thus, it is essential to measure an electron energy loss spectrum after energy correction for solving the problem describe above.

The purpose of the present invention is to provide an apparatus and a method for measuring electron energy loss spectrum at high precision and high accuracy with an apparatus combining a TEM or an STEM with an EELS.

The present invention provides an EELS apparatus provided with an electron beam detector which comprises multiple pixels, and measures a spectrum of an electron beam which has transmitted through a specimen, and a controller which controls the position of the electron beam incident to the electron beam detector such that the electron beam detector measures a spectrum with a know dispersion, a position deviation pixel number between a pixel position for a peak appeared on the spectrum measured by the electron beam detector, and a reference pixel position designated as a reference position on the electron beam detector is measured, the position deviation pixel number is converted into a control factor for controlling the position of the electron beam such as a voltage value or a current value based on the spectrum dispersion, and the position deviation is corrected based on the control factor.

The electron energy loss spectrum measuring method of the present invention features that after an operation for correcting the peak position deviation of the spectrum is conducted with the EELS apparatus provided with the peak position control apparatus for correcting a peak position in a spectrum, the electron energy loss spectrum is measured at high precision.

In addition, the electron beam detector detects zero-loss peak where the spectrum intensity is at the maximum, and the controller corrects such that the peak position of the zero-loss peak matches a reference peak position of the electron beam detector, thereby correcting spectrum energy at high precision in a short period, resulting in measuring an electron energy loss spectrum at high precision and high accuracy. Even if the zero-loss peak does not exist on the electron beam detector, the controller can control such that the zero-loss peak appears on the electron beam detector, and then the controller can again control such that the zero-loss peak matches the reference pixel position of the electron beam detector. Thus, the energy correction takes a short period, and the measuring is conducted at high precision and at high accuracy when a wider range of electron energy loss spectrum is measured.

An STEM or a TEM provided with the EELS according to the present invention has a controller comprising a memory for storing a result of spectrum measuring by the electron beam detector, a data base for storing a database for core loss energy or plasmon loss energy for elements to be analyzed, measuring conditions and the like, and a central controller for controlling the spectrum measuring and peak position control operation. In addition, the STEM provided with the EELS has a controller comprises a memory for storing a spectrum measured by the electron beam detector, an energy filter controller for controlling the peak position on the electron beam detector, and an STEM controller for controlling the electron beam position on a specimen.

An operation is repeated such that a spectrum is measured after the energy correction, then measuring is switched to another location, and again, a spectrum is measured after the energy correction in the electron energy loss spectrum measuring method of the present invention where locations for measuring are changed sequentially on a specimen. With this method, the electron energy loss spectrum is measured at high precision and at high accuracy when multiple locations are measured on a specimen.

The EELS apparatus of the present invention includes at least two electron beam detectors comprising an electron beam detector for detecting a zero-loss to correct energy, and an electron beam detector for measuring an electron energy loss spectrum.

The present invention allows automatically adjusting the focus of a spectrum.

DESCRIPTION OF THE PREFERRED EMBODIMENTS

The following section describes embodiments of the present invention while referring to figures.

Figure 1A:
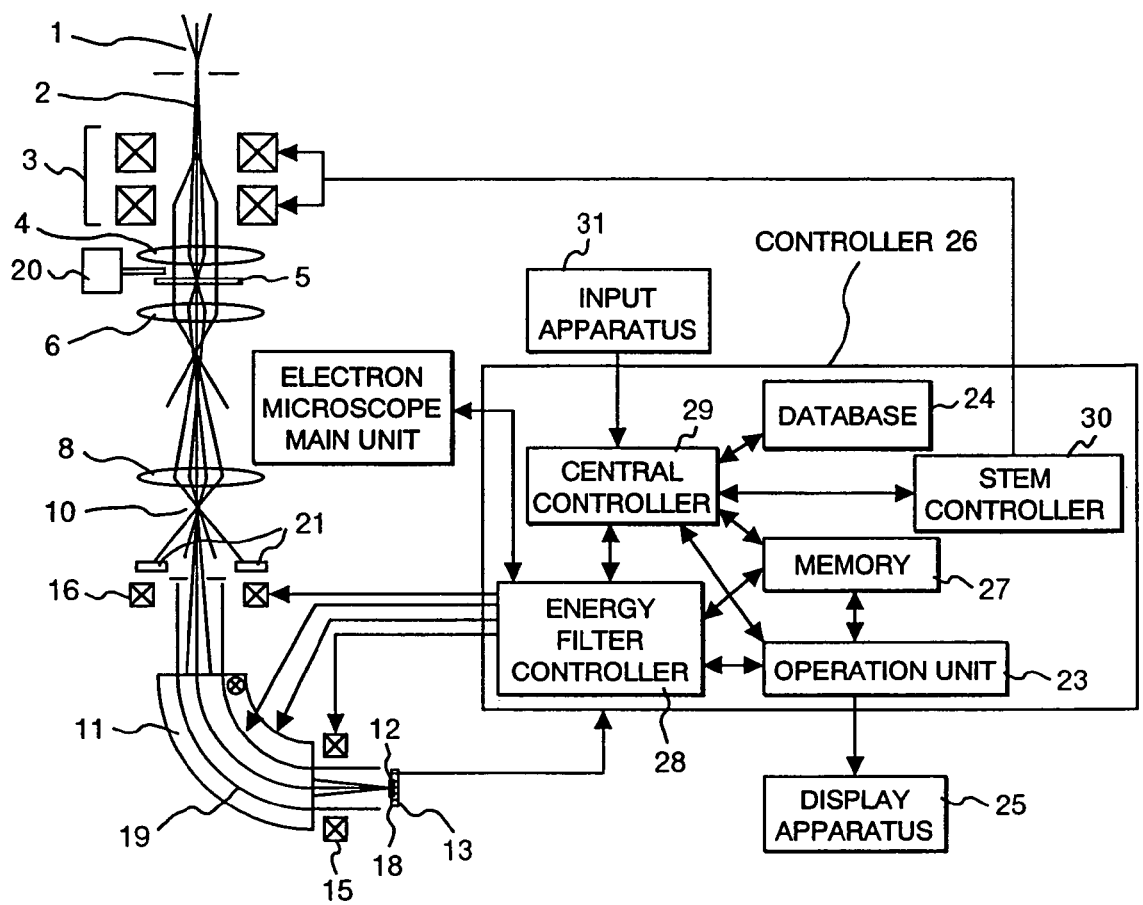
FIG. 1a is a structural schematic for a main part of an embodiment of the present invention.
Figure 1B:
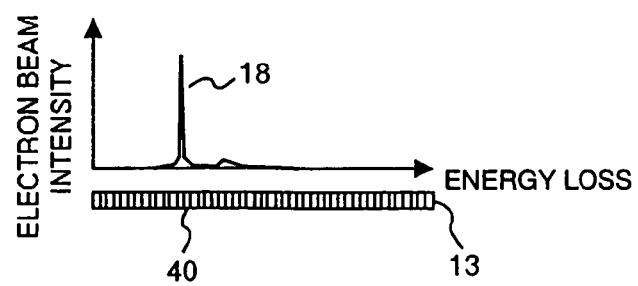
FIG. 1b is a drawing showing a relationship between an electron energy loss spectrum and an electron beam detector for detecting it.

FIG. 1 is a structural schematic of a major part of a scanning transmission electron microscope (also referred as electron microscope in this document). A part from an electron beam source 1 to a Z contrast detector 21 is described as an electron microscope main unit, and a part from a magnetic field lens 16 for adjusting focus to an electron beam detector 13 is described as an EELS apparatus in FIG. 1.

A cold cathode field emission type electron beam source can be applied to the electron beam source 1. An electron beam scan coil 3 deflects an electron beam 2 generated from the electron beam source 1. A magnetic field above objective lens 4 converges the deflected electron beam 2 on a face of a specimen 5, and the electron beam 2 scans on the specimen surface. The objective lens and a projection lens apply a lens effect to the electron beam which has transmitted through the specimen, and an object point 10 is formed.

The electron beam from the object point 10 comes into a magnetic field sector 11 in a fan shape. The magnetic field of a magnet constituting the magnetic filed sector 11 forms a magnetic field space perpendicular to the paper of FIG. 1. The electron beam which comes into the magnetic field sector 11 is deflected by 90 degree, is made into a energy spectrum, and is focused on the energy dispersion surface 12. The energy dispersion surface 12 exists on an electron beam detector 13 in the present embodiment.

The spectrum formed on the energy dispersion surface 12 is about 1 eV/μm in the present embodiment when the rotation radius of an electron beam of an electron spectrometer 11 is 100 mm. A magnetic lens 15 for magnifying the spectrum magnifies it by 100 times. A magnetic field of an electromagnetic field lens 16 is adjusted to focus the spectrum on the electron beam detector 13. As the result, an electron energy loss spectrum 18 projected on the electron beam detector 13 becomes 0.01 eV/μm. A multi-channel plate array with 25 μm/channel is used as the electron beam detector 13 provides 0.25 eV/channel.

A controller 26 comprises a central controller 29, an energy filter controller 28, an operation unit 23, a database 24, a memory 27, and a STEM electron beam position controller 30, and the controller 26 is connected with an input apparatus 31 into which an operator enters measuring conditions and the like, and a display apparatus 25 for showing a spectrum, an electron microscope image, an element distribution image and the like.

[Electron Energy Loss Spectrum Measuring]

The following section describes an operation in the controller 26 while measuring a spectrum.

When an operator uses the input apparatus 31 to enter an element to be observed, the central controller 29 extracts corresponding element information from the database 24, and provides the energy filter controller 28 with measuring conditions specific to individual elements included in the element information. The energy filter controller 28 controls a magnetic field lens for adjusting focus 16, a magnetic lens 15 for magnifying the spectrum, a drift tube 19, and a magnetic field sector 11, and makes an electron beam in an energy range including energy specific to the element incident to the electron beam detector 13. Electron intensity signals corresponding to individual channels of the electron beam detector 13 represent an electron energy loss spectrum. The electron beam intensity signals from the electron beam detector 13 enter the operation unit 23, and background correction for the spectrum, gain correction for the electron beam detector and the like are conducted in the operation unit 23. The spectrum after the operation is stored in the memory 27, and is simultaneously shown on the display apparatus 25. The operator can obtain a spectrum with these series of operations.

[Energy Correction for Spectrum]

An exposure time (time for receiving an electron beam) of the electron beam detector 13 extends if a spectrum is obtained at high sensitivity. For example, about five seconds of the exposure time can obtain an electron energy loss spectrum caused by electrons which have lost energy to excite K shell electrons of nitrogen. If the energy of the spectrum shifts in the exposure time, it is required to correct the energy of the spectrum. The energy shift of a spectrum means that an electron trajectory in the electron microscope or the energy filter is disturbed, electrons with the equivalent energy come into different channels of the electron beam detector 13, and the energy value shifts while the shape of a measured spectrum is being maintained.

The present embodiment measures a spectrum while correcting this type of an energy shift. The overview of the spectrum measuring steps includes steps of (1) an operator enters measuring conditions, (2) an electron energy loss spectrum is measured in a determined exposure time following the measuring conditions, and (3) a peak of zero-loss electron or an inner shell electron excitation peak of a known element is used to correct the energy. A zero-loss electron is an electron of electron beams which have transmitted through a specimen, and have the same energy as the incident electron beams. (4) Measuring continues after returning to (2). Namely, the measuring continues consecutively in the sequence of (1), (2a), (3a), (2b), and (3b). The following section describes the individual steps.

(1) First, an operator enters an element to be observed and a timing for correcting energy, for example, a time interval for correcting or a spacing between observed points. (2a) As described in "Electron energy loss spectrum measuring" before, the central controller 29, the data base 24, and the energy filter 28 operate to make an electron beam in an energy range including energy specific to the element come into the electron beam detector 13. The electron beam detector 13 receives the electron beam for a time calculated from the exposure time and the timing for correcting energy specified by the operator. The operation unit 23 receives the received electron beam intensity signal, and the operation unit conducts the background correction for the spectrum and the gain correction for the electron beam detector 13. The spectrum after the operation is stored in the memory 27, and is shown on the display apparatus 25. (3a) The following section describes an energy correction while using the peak of the zero-loss electron. The energy filter controller 28 adjusts voltage of the electron beam source 1 or the drift tube 19 such that the peak of the zero-loss electrons appears near a reference pixel position (also referred as base pixel position. Described in detail later) specified by the operator on the electron beam detector 13, and the electron beam detector 13 measures the intensity of the electron beam. The condition for adjusting such that the peak of the zero-loss electrons appears near the reference pixel position is a condition that the peak of the zero-loss electron matches the reference pixel position when there is no interference. The operation unit 23 receives the measured electron beam intensity signal, measures a deviation between the reference pixel position and the peak position of the zero-loss electrons, and calculates conditions for controlling the electron beam source 1, the drift tube 19, the magnetic field sector 11, or what can control the electron beam position such that the deviation becomes zero. The calculated condition is sent to the central controller 29, and the central controller 29 provides the energy filter controller 28 with a control signal. As the result, trajectories of the electrons in the electron microscope and the energy filter are corrected, and the energy correction for the spectrum is completed. Then, an operation (2b) equivalent to the (2a) described above is conducted, and the measuring continues.

(3') The following section describes an energy correction while using a peak which appears when inner shell electrons specific to an element are exited. In this case, the measuring procedure continues in a sequence of (1), (2a), (2b), (3b'), (2c), (3c'), and (2d). The following section specifically describes an operation in (3b'). The operation unit 23 receives the electron beam intensity signal (designated as Ib) measured in (2b). The operation unit 23 receives the electron beam intensity signal (designated as Ia) from the memory 27, the spectrum of Ib is compared with the spectrum of Ia, and a position deviation of the peak position specific to the element is measured. The operation unit 23 calculates a condition for controlling the electron beam source 1, the drift tube 19, the magnetic field sector 11, or what can control the electron beam position such that the deviation becomes zero. The calculated condition is sent to the central controller 29, and the central controller 29 provides the energy filter controller 28 with a control signal. As the result, trajectories of the electrons in the electron microscope and the energy filter are corrected, and the energy correction for the spectrum is completed. Then, an operation (2c) equivalent to the (2a) described above is conducted, and the measuring continues.

The operator can obtain a spectrum applied with the energy correction with these series of operation.

[Reference Pixel Position of Energy on Electron Beam Detector 13]

The electron beam detector 13 comprises multiple channels, an example of the number of the channels is 1024, and it may be less than or more than 1024. The zero-loss electrons are observed as a peak on the electron energy loss spectrum 18 formed on the energy dispersion surface 12. FIG. 1(*b*) shows a positional relationship between the electron energy loss spectrum 18 formed on the energy dispersion surface 12, and the electron beam detector 13. Usually, the film thickness of a specimen for a transmission electron microscope is thin, and if the film thickness is 100 nm or less, for example, the peak intensity caused by the zero-loss electrons is at the maximum in the electron energy loss spectrum 18. Since the zero-loss electrons have no energy loss, the peak position of the zero-loss electrons is at the zero-point on horizontal axis, which becomes the reference point of energy when the electron energy loss spectrum 18 is drawn as in FIG. 1(*b*) where the energy loss is the horizontal axis, and the electron beam intensity is the vertical axis.

The operator determines the reference pixel position of the energy on the electron beam detector 13, namely, reference pixel position 40 (also referred as reference channel position) before hand in the present embodiment (See FIG. 1(*b*)). There is no restriction on the reference pixel position as long as it exists on the electron beam detector 13. However, considering the electron energy loss spectrum 18 is measured, the electron energy loss spectrum 18 is measured in a wider loss energy range when the reference pixel position 40 is set on a higher energy side of the electron energy loss spectrum 18 detected by the electron beam detector 13. The peak of the zero-loss electron is moved to the reference pixel position 40. As a mean of the movement, the electron beam source 1, the drift tube 19, or the magnetic sector 11 is used for the control. As described later in detail, an operator simply selects one button or one key on the input apparatus 21, and the controller 26 automatically moves the zero-loss peak in the present embodiment. This operation completes the automatic energy zero-point correction for the electron energy loss spectrum measurement. After completing the zero-point correction, when the electron energy loss spectrum 18 is measured, an electron beam detected in the same channel always has the same energy.

The following section describes the energy reference position when the electron energy loss spectrum for an element which has a large energy loss is measured. When the electron beam detector 13 comprises 1024 channels, and the dispersion of the electron energy loss spectrum 18, namely, the energy range detected by a single channel, is 0.25 eV/channel, for example, the energy range which can be detected by the electron beam detector 13 is 256 eV. An electron which transmitted through a specimen excites inner shell electrons of atoms constituting the specimen, and loses energy, and when an element whose energy loss is 256 eV or more (energy loss for exciting the K shell electron of nitrogen is 400 eV, and that for the K shell of oxygen is 532 eV, for example) is measured, the peak of the zero-loss electron moves outside of the electron beam detector 13. It moves to the left side of the electron beam detector 13 in FIG. 1(*b*). When an element to be measured is nitrogen, after the energy zero-point correction described before is applied, the voltage of the drift tube 19 increased by 400 eV is applied, the energy of electrons coming into the reference pixel position 40 becomes 400 eV. The electron energy loss spectrum measured after this operation presents 400 eV of the energy loss at the reference pixel position 40, and is an electron energy loss spectrum including a peak caused by exciting the K shell electron of nitrogen. For these series of operation, the operator simply selects an element to be measured, and instructs the start of measuring, and the controller automatically conducts the other operations. The detail is described later.

The following section described an embodiment for a method for measuring electron energy loss using the present embodiment.

FIG. 2 is used to show an example of processing for measuring the electron energy loss spectrum.

Conventionally, an operator sets a specimen on a scanning transmission electron microscope (STEM), adjusts the optical axis of the STEM, (1) specifies a location to be analyzed on the specimen, (2) adjusts the focus, (3) corrects the energy zero-point of a spectrum, (4) specifies an element to be analyzed, or an energy range to be measured, and (5) measures a spectrum.

With the present embodiment of the present invention, an operator simply sets a specimen on a scanning transmission electronic microscope (STEM), adjusts the optical axis of the STEM, (1) specifies a location to be analyzed on the specimen, and (2) specifies an element to be analyzed, or an energy range to be measured, and the controller 26 follows the instruction of the operator, and controls the other operations comprising (3) adjusting the focus, (4) correcting the energy zero-point of a spectrum, (5) adjusting measuring conditions corresponding to the element to be measured, namely, adjusting the voltage for the drift tube 19 and the current for the magnetic lens 15 for magnifying the spectrum based on the EELS table, (6) correcting the energy of the spectrum, and (7) measuring a spectrum.

(1) A button for selecting automatic focusing, (2) a button for detecting the peak of the zero-loss electrons on a spectrum, and automatically correcting the energy zero-point of the spectrum, (3) buttons with icons showing element symbols for specifying an element to be analyzed, and (4) a button for selecting the energy shift correction for the spectrum should be selectable on a monitor screen of the input apparatus 31 for these operations, and icons for illustrating the individual operations on the monitor, for example, in the present embodiment. Especially, the display of the button for selecting automatic focusing and the button for automatically correcting the energy zero-point is a characteristic of the apparatus of the present embodiment. The following section describes each automatic processing under the control of the controller 26.

[Automatic Focusing for Spectrum]

Adjusting the optical axis of the STEM makes zero-loss electrons incident to the electron beam detector 13. If the focus of the spectrum is not adjusted, the half-width of the zero-loss electrons peak becomes wider, and takes a shape shown in FIG. 2(b). When an operator selects the button for adjusting the automatic focusing shown on the monitor screen of the input apparatus 31, the automatic focus adjusting is completed automatically in the present embodiment. The following section describes a basic principle of the automatic focus adjusting.

The electron beam detector 13 detects the zero-loss electrons while sequentially changing magnetic field intensity of the magnetic field lens for adjusting focus 16. A condition where the peak of the half width caused by the zero-loss electrons is minimum and/or a condition where the peak intensity of the zero-loss electrons is maximum is selected from the magnetic field intensity changed sequentially, and a corresponding magnetic field intensity is designated as an optimal condition for the focus of the spectrum.

The controller 26 conducts the following processing to realize the principle described above as indicated in FIG. 2(c). (1) When an operator selects the automatic focus adjusting from the input apparatus 31, (2) the central controller 29 sets a control range and a current step for the lens current for changing the magnetic field intensity of the magnetic field lens for adjusting focus 16, and the exposure time for measuring the spectrum with the electron beam detector 13, and provides the energy filter controller 28 with the individual measuring conditions. (3) The energy filter controller 28 follows the entered conditions to set the lens current and the magnetic field of the magnetic field lens for adjusting focus 16, (4) the electron beam detector 13 measures the incident electron beam intensity for the set exposure time. (5) The operation unit 23 receives the measured electron beam intensity, and stores it into the memory 27 after the background correction and the gain correction of the electron beam detector 13. (6) When the memory 27 notifies the central controller 29 that the measuring was completed, and (7) the energy filter controller 28 receives new conditions for setting the magnetic field lens for adjusting focus 16. (8) In the following procedure, the spectrum measuring is conducted with a new lens current. (9) In this way, the condition where the half-width of the zero-loss peak is minimum and/or the condition where the zero-loss peak intensity is maximum in the specified lens current range are selected from data stored in the memory 27, and the conditions are set through the energy filter controller 28 as the current value for the magnetic field lens for adjusting focus.

[Energy Zero-Point Correction for Spectrum]

The reference pixel position 40 is set on the higher energy side on the electron beam detector 13. This operation is conducted in a situation such as initial installation of the apparatus, and is not required each time when a specimen is set. When the peak position of the zero-loss electrons is different from the reference pixel position 40, an operator simply selects the button for automatically correcting the energy zero-point displayed on the monitor screen of the input apparatus 31 in the present embodiment. When the button for automatically correcting the energy zero-point is selected, the controller 26 automatically processes the following operation, and completes the energy zero-point correction. The following section shows and describes the energy zero-point automatic correction in detail in FIG. 2(e).

First, (1) an operator selects the energy zero-point correction from the input apparatus 31, (2) the central controller 29 provides the energy filter controller 28 with conditions for measuring the zero-loss electrons, for example, voltage conditions for the drift tube 19, (3) the energy filter controller 28 sets the voltage provided for the drift tube 19. (4) When the electron beam detector 13 measures the peak position of the zero-loss electrons, the operation unit 23 receives the electron beam intensity signal. When the zero-loss electrons are not detected, the voltage for the drift tube 19 is changed, and the electron beam detector 13 measures again. The voltage for the drift tube 19 is adjusted until the zero-loss electrons are measured. The operation (1) through (4) is an operation to retrieve the zero-loss electron automatically.

Figure 2A:
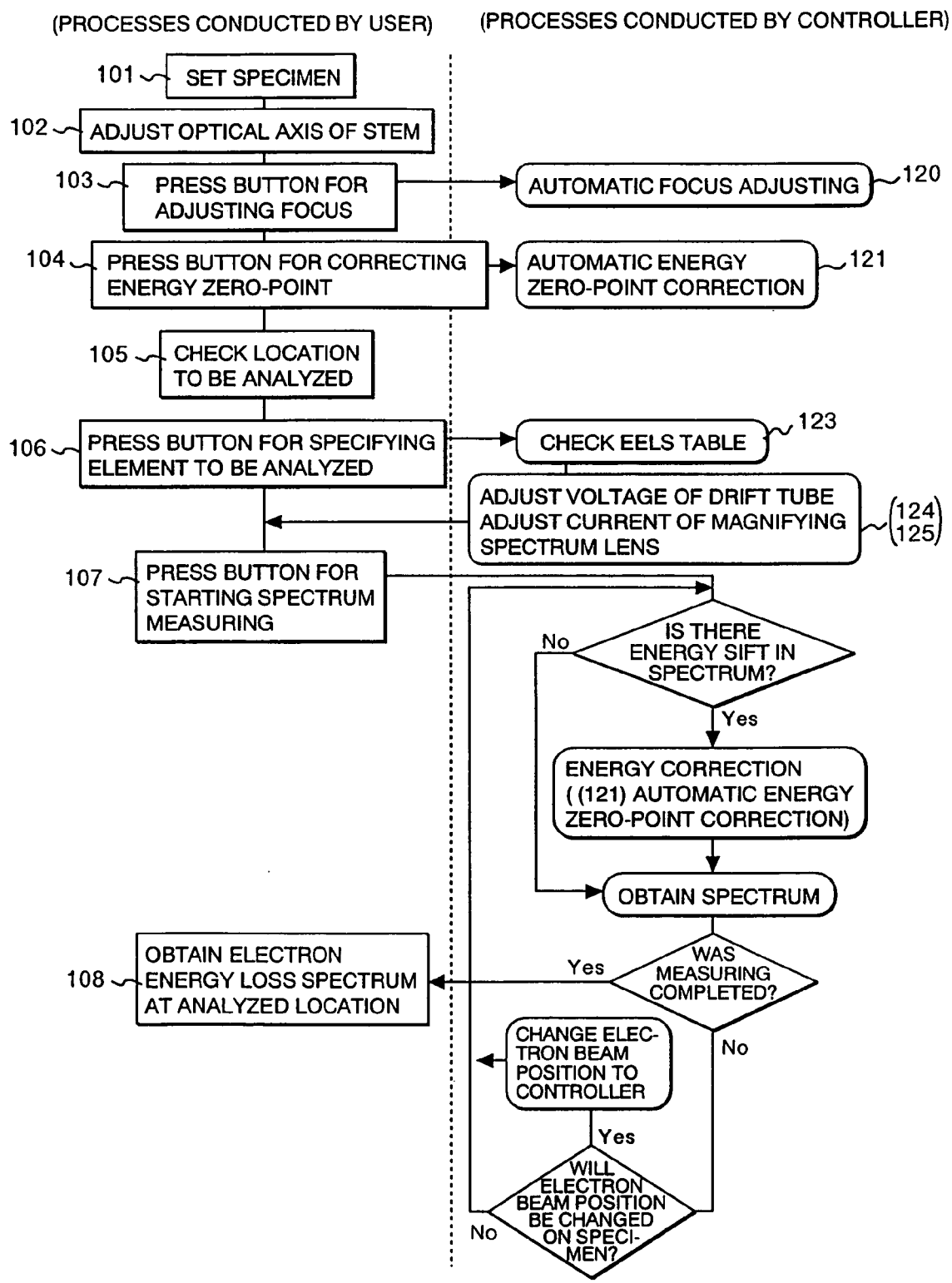
FIG. 2a is a drawing for showing an example of a processing for obtaining an electron energy loss spectrum.
Figure 2B:
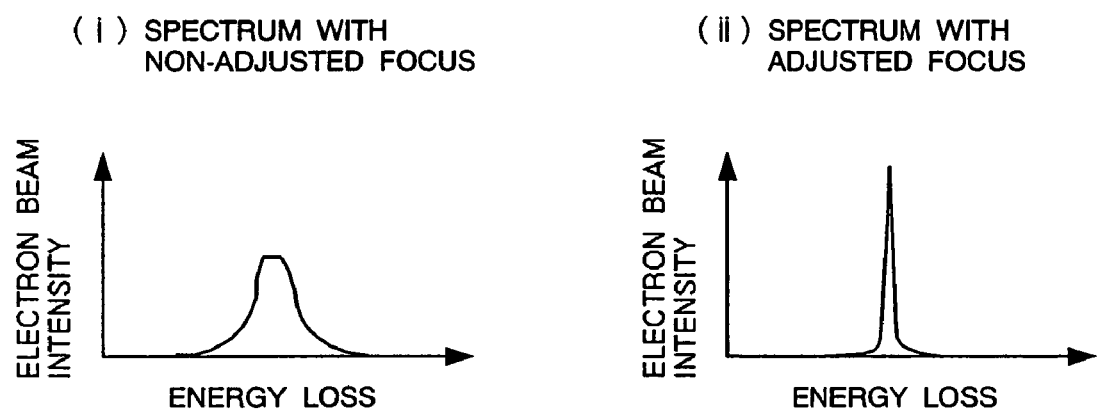
FIG. 2b is a drawing for showing an example of a state where the focus of an electron energy loss spectrum is not adjusted and a state where the focus is adjusted.
Figure 2C:
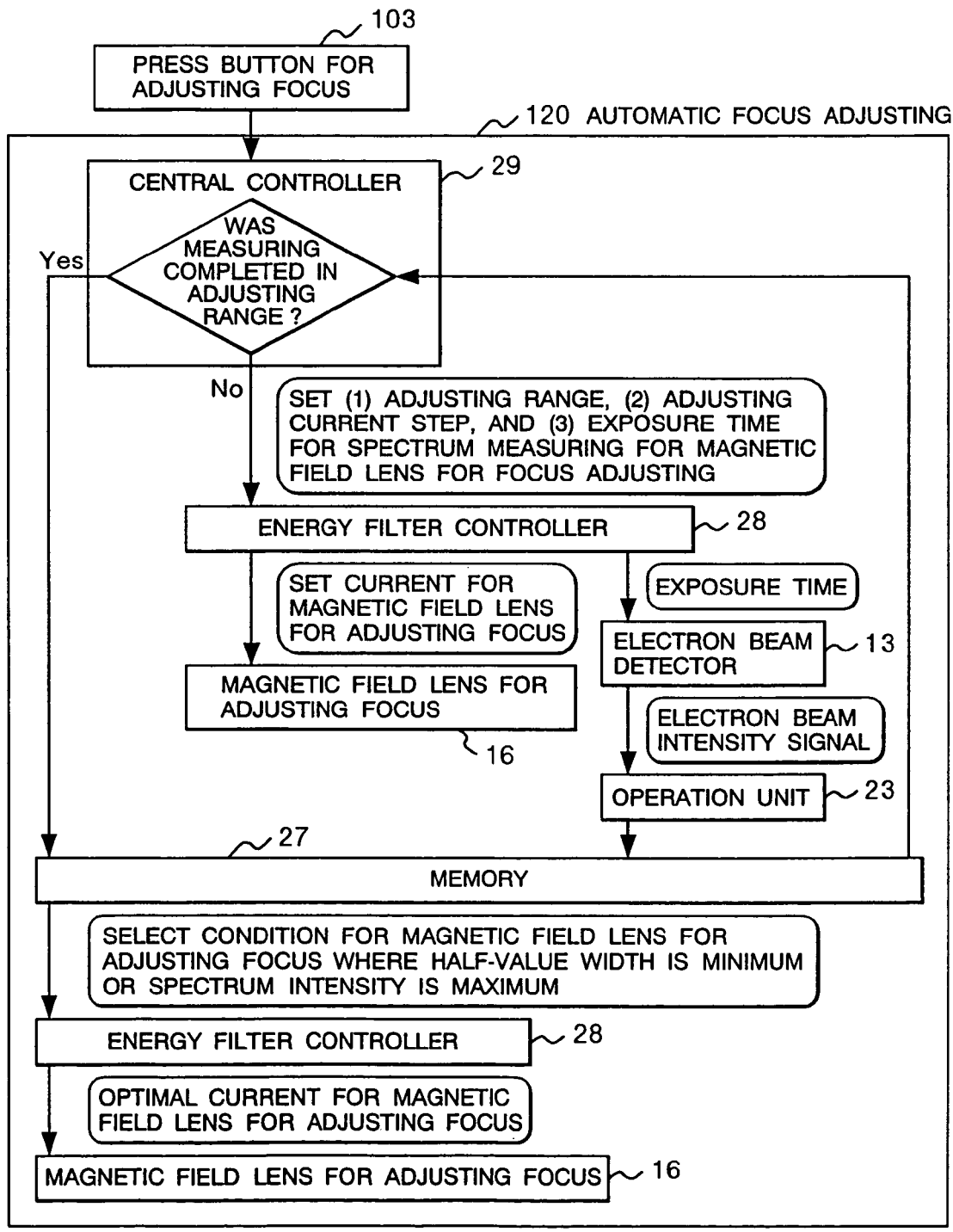
FIG. 2c is a drawing for showing an example of a processing for automatically adjusting the focus of an electron energy loss spectrum.
Figure 2D:
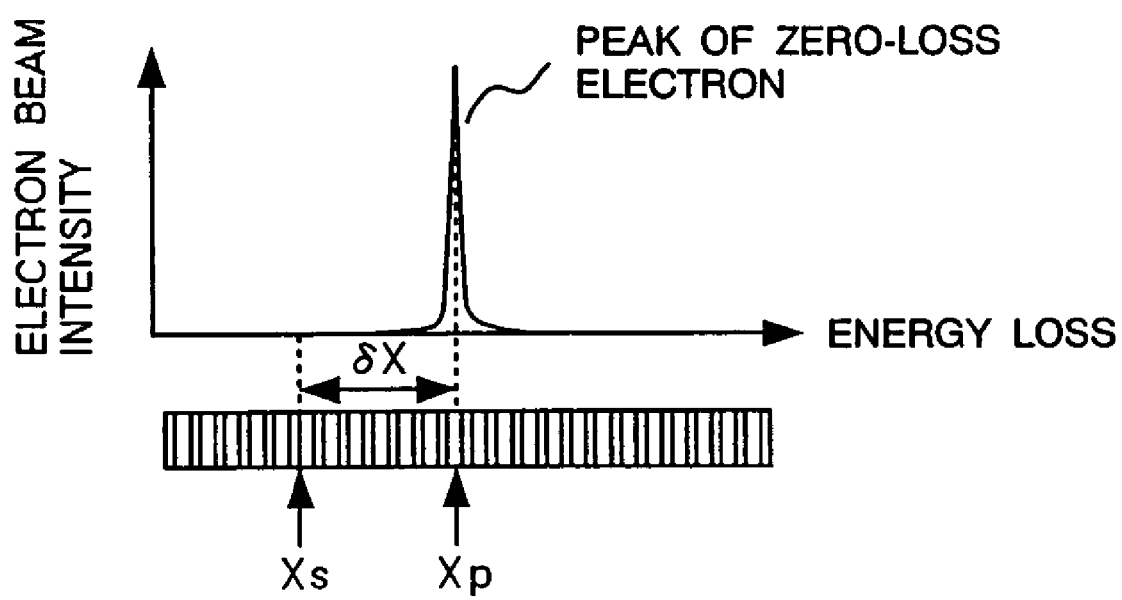
FIG. 2d is a drawing for showing an example of a relationship between a peak position of zero-loss electrons and a reference pixel position of an electron beam detector.
Figure 2E:
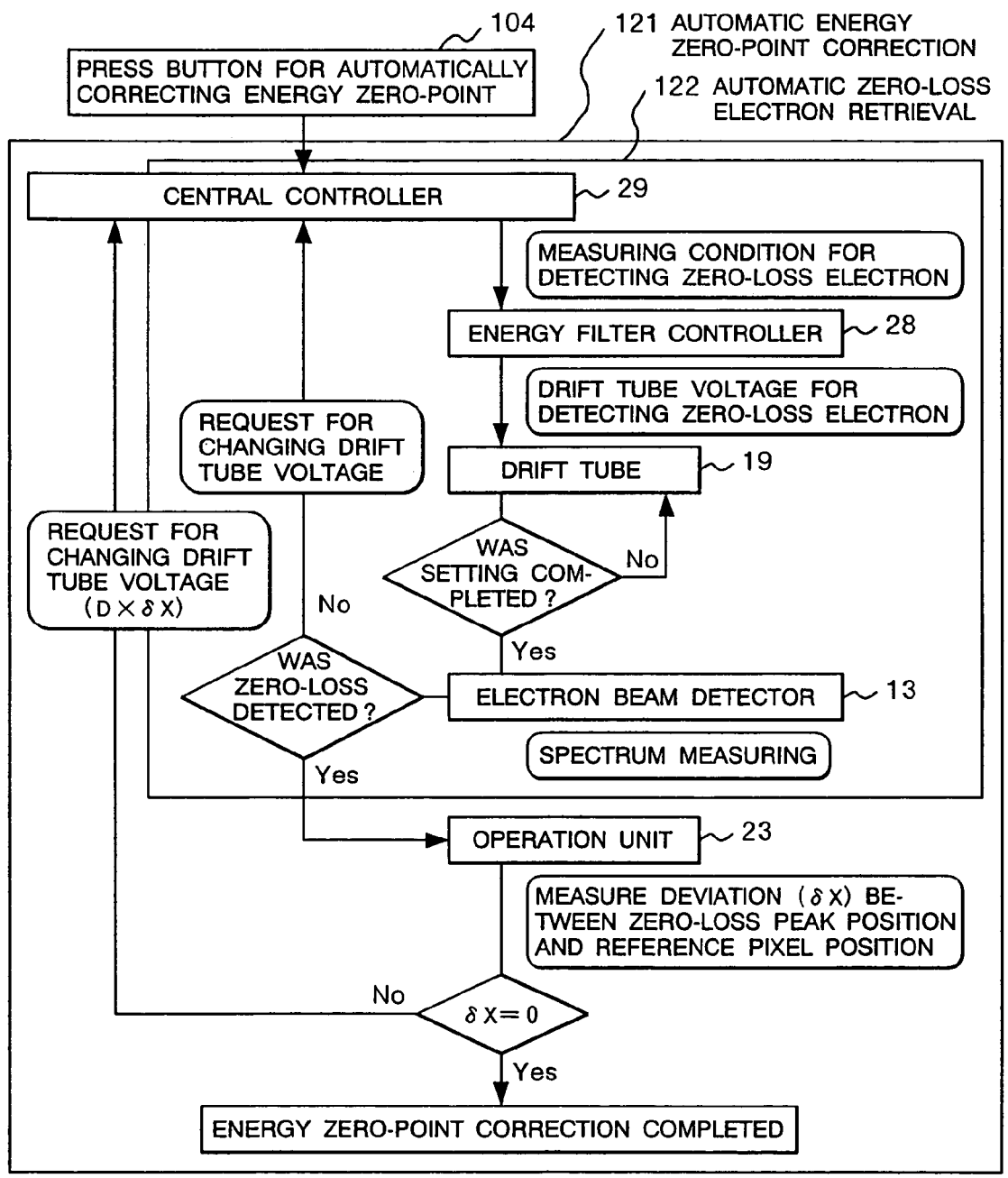
FIG. 2e is a drawing for showing an example of a processing for automatically adjusting an energy shift on an electron energy loss spectrum.

Then, (5) the operation unit 23 compares the peak position of the zero-loss electrons (designated as Xp channel, see FIG. 2(d)) with the reference pixel position on the electron beam detector 13 (designated as Xs), and calculates the deviation between them ($\delta X = Xp - Xs$), and the energy zero-point correction is completed when $\delta X = 0$. If $\delta X$ is not zero, (6) the operation unit 23 converts the deviation of the spectrum into energy ($\delta E = D \times \delta X$ (eV)) based on the energy dispersion D (unit: eV/channel) of the spectrum, and provides the central controller 29 with $\delta E$, (7) the central controller 29 converts the deviation of the energy $\delta E$ into a control factor for the energy filter controller to control the trajectory of the electrons in the electron microscope or the energy filter. Specifically, the voltage of the drift tube 19 should be increased by $\delta E$. (8) When the energy filter controller 28 receives the converted control factor, the electron beam source 1 or the drift tube 19 operates under new conditions. With this automatic energy zero-point correction, the peak of the zero-loss electrons matches the reference pixel position on the electron beam detector 13. Making the drift tube voltage after the adjusting appears to be 0 eV, the impressed drift tube voltage is directly read as energy loss (eV) of the electron energy loss spectrum when the following measuring conditions are adjusted.

[Adjusting Measuring Conditions Corresponding to Element to be Measured]

Figure 2F:
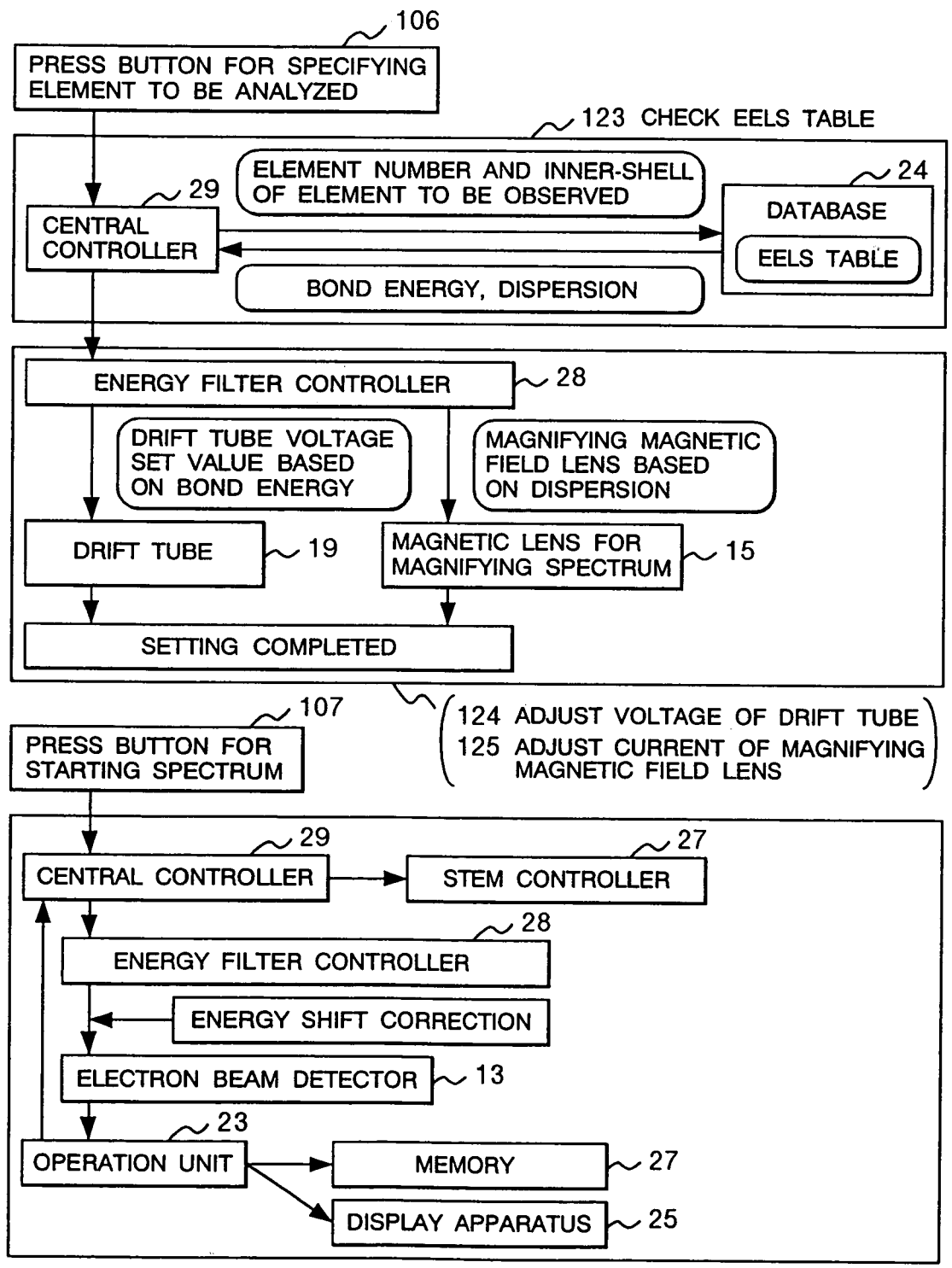
FIG. 2f is a drawing for showing an example of a processing for adjusting measuring conditions for measuring an electron energy loss spectrum for an element selected by an operator.

When the electron energy loss spectrum of an element specified by an operator is measured, it is required to adjust optimal measuring conditions for individual elements to be measured, and the controller 26 is used for adjusting automatically as described in FIG. 2(f).

Figures 2G, 2H:
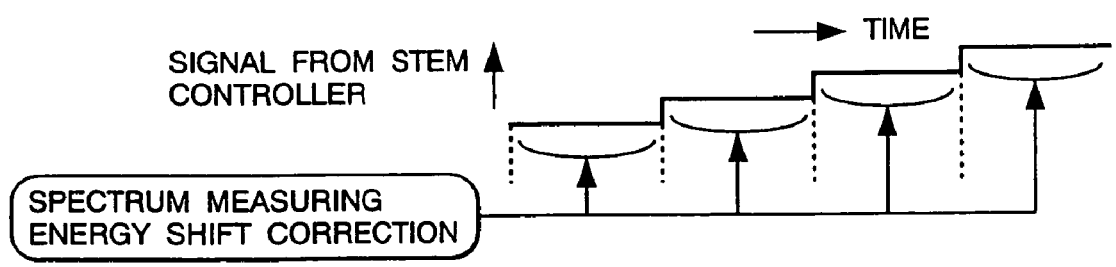
FIG. 2g is a drawing for showing an example of data stored in an EELS table.
FIG. 2h is a drawing for showing an example of a relationship between a signal level of an STEM controller, and timings for spectrum measuring and an energy shift correction in order to measure an electron energy loss spectrum while moving an electron beam position on a specimen.

First, (1) an operator specifies an element shown on the monitor screen of the input apparatus 31, (2) the central controller 29 obtains data corresponding to the element entered from the EELS table stored in the database 24. An example of the EELS table for nitrogen and oxygen is shown in FIG. 2(g). (a) Element number, (b) element name, (c)

inner shell of electrons excited by the incident electrons, (d) bond energy of the inner shell electrons (unit is eV), and (e) optimal energy dispersion for measuring spectrum (unit is eV/ch) are stored in the table. (3) The central controller 29 determines the voltage impressed on the drift tube 19 with the voltage (V0) of the drift tube after energy zero-point correction as a reference, namely, with the energy loss as 0 eV referring to the bond energy of the element to be measured. When the bond energy is E1 (eV), for example E1=400 for nitrogen, a voltage V0+E1 volt is a new voltage impressed on the drift tube 19. Also set current value for the magnetic field magnifying lens 15 is determined for controlling the energy dispersion optimal for measuring the spectrum. (4) The central controller 29 provides the energy filter controller 28 with the voltage impressed on the drift tube 19, and the set current for the magnetic lens 15 for magnifying the spectrum.

Then, (5) after setting the measuring conditions is completed, the operator selects the button for staring spectrum measuring shown on the monitor screen of the input apparatus 31. (6) The electron beam detector 13 measures the spectrum for the set exposure time, the operation unit 23 applies the background correction and the gain correction for the electron beam detector 13, the memory 27 stores the spectrum, and the spectrum is shown on the display apparatus 25. For example, after the setting described above, the electron energy loss spectrum of nitrogen is measured, a peak caused by the excitation of the K shell electrons of nitrogen is observed at the reference pixel position on the electron beam detector 13.

As described above, an operator simply presses the button for specifying an element to be measured, and then presses the button for starting measuring the spectrum to measure the spectrum.

[Energy Correction Processing for Spectrum and Measuring Spectrum]

When a spectrum is measured, the energy of the spectrum is corrected, and a location to be measured is moved properly based on the operator's setting as follows.

The energy correction for a spectrum is used when a spectrum is measured for a long period. Before a spectrum is measured, though the energy zero-point correction of a spectrum described before is conducted, trajectories of electrons in the electron microscope and the energy filter may change because of an effect of a disturbance of a external magnetic field and the like when the measuring requires a long period. In that case, electron beams detected in the same channel of the electron beam detector 13 have different energy, and the energy zero-point correction is required again. The energy zero-point correction is always available as long as the electron energy loss spectrum is being measured in the present embodiment. The energy zero-point correction is conducted in the same way as the energy zero-point correction for a spectrum described before. An operator can set a time interval for conducting the energy zero-point correction before hand as the timing for conducting the energy zero-point correction. The spectrum measuring continues with the energy filter control conditions after the energy zero-point correction as a new reference. It is possible to use the STEM controller 30 in the controller 26 to conduct the energy zero-point correction each time when the position of the electron beam on a specimen moves.

For a position deviation of the spectrum, the following method is available in addition to the energy zero-point correction described above. Note that this method is possible only when the electron beam remains to the same location on a specimen. As a spectrum is measured at the same location, the peak position appearing on the spectrum, namely, energy loss, is the same, and the pixel position of the electron beam detector 13 which detects the peak is the same as well. However, the spectrum on the electron beam detector 13 shifts in the direction of energy dispersion due to an interference such as an external magnetic field and the like, the pixel position of the electron beam detector 13 for detecting the peak appearing on the spectrum deviates. Comparing the pixel position for detecting the peak with the result of a spectrum measured immediately before allows measuring the shift of the spectrum in pixel as a deviation. The deviation is converted into a voltage or a current for controlling the drift tube 19 or the magnetic field sector 11 for example, and is corrected. A core loss peak which exciting inner shell electrons generates on the electron energy loss spectrum is observed as a small peak or an edge on a background with high electron beam intensity. As a mean for determining a pixel position for the small peak on the electron beam detector 13 at high precision, (1) differentiating an obtained spectrum by energy loss, or (2) representing the vertical axis in logarithm are selectable in the present embodiment. By measuring a spectrum in this way it is possible to measure an electron energy loss spectrum at high accuracy and at high precision.

[Moving Location to be Beasured]

An electron beam incident to a specimen is converged into about 1 nm or less in diameter in a scanning transmission microscope, and scans on a specimen in two dimensions. The electron beam scan coil 3 of the electron microscope is used to control the scan of the electron beam, and the controller 26 controls the electron beam scan coil 3. The electron beam energy loss spectrum is measured while sequentially moving to locations to be measured set by an operator before measuring in the present embodiment. It is possible to conduct the energy zero-point correction described before each time when the location to be measured is moved when an operator is set so before measuring. The operation above is described while showing it in FIG. 2(h).

FIG. 2(h) shows the electron beam position control on a specimen by the STEM controller 30, and the timing for the spectrum measuring and the energy shift correction by the electron beam detector 30. Since signal level provided by the STEM controller is constant until the energy shift correction and the spectrum measuring are completed, the electron beam remains at the same position on the specimen. When the energy shift correction and the spectrum measuring are completed, the central controller 29 provides the STEM controller 30 with an instruction for increasing the signal level by one step. The increase of the output signal level by one step from the STEM controller 30 corresponds to a travel of the electron beam on the specimen by a prescribed distance. The spectrum is measured while moving among locations to be measured under this control.

Figure 3A:
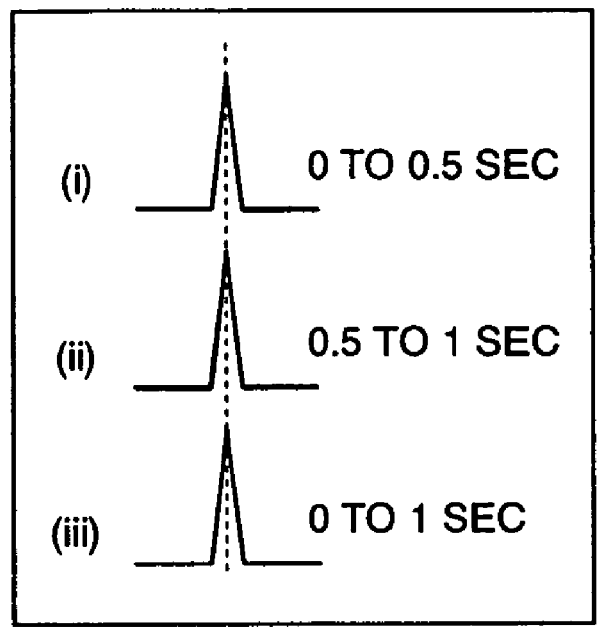
FIGS. 3a and 3b show an example of an electron energy loss spectrum of core loss elections.

FIG. 3(a) shows an example of an electron energy loss spectrum caused by inner shell excitation of elements constituting a specimen measured by the apparatus of the present embodiment. A peak shown in FIG. 3(a) appears on the electron energy loss spectrum because the electron beam excites the inner shell electrons of atoms when the electron beam transmits through the specimen, and the electron beam loses energy specific to the element. Since the dispersion of the spectrum is 0.25 eV/µm, a spectrum whose measuring accuracy at the peak position is 0.25 eV can be measured as shown in FIG. 3(a).

Examples of information on the core loss peak 27 stored in the database 24 include 721 eV of bonding energy for L2 shell electron and 708 eV of bonding energy for L2 for iron (Fe). It may be 600 to 800 eV as an energy range including EL2: 721 eV and EL3: 708 eV. The energy dispersion is 0.3 eV/ch.

Figure 3B:
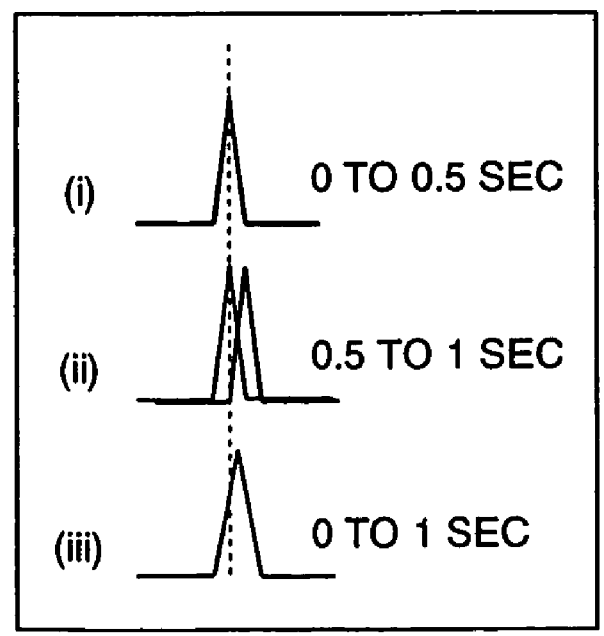
Figure 4A:
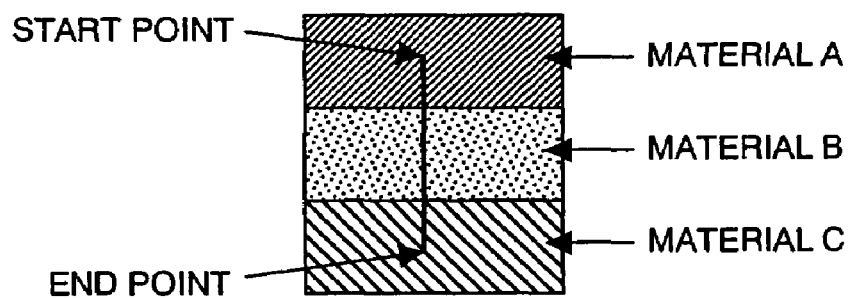
FIGS. 4a through 4d show a schematic for laminated materials, and an example of consecutively measuring an electron energy loss spectrum between two points on the materials.
Figure 4B:
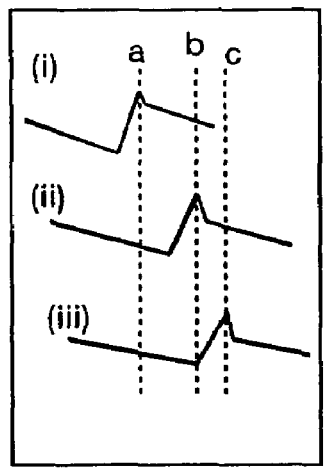
Figure 4C:
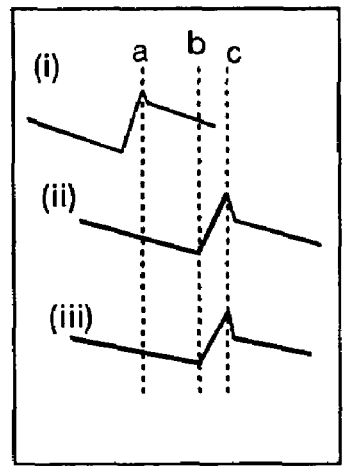
Figure 4D:
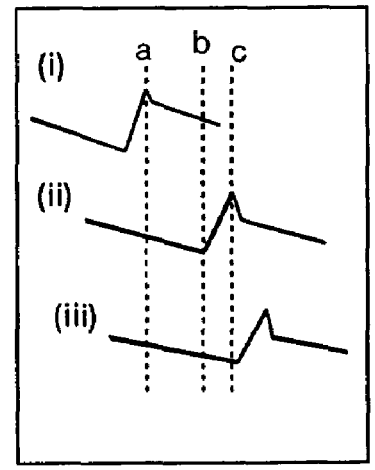

Though one multi-channel plate array is used as the electron beam detector 13 in the present embodiment, it is possible to use two multi-channel plate arrays, where one is used for measuring the electron energy loss spectrum, the remaining one is placed to measure a zero-loss, always detects a change in the zero-loss peak position on the multi-channel plate array, and uses the controller 26 to correct energy so as to return the peak position to the reference pixel position when the zero-loss peak position deviates from the reference pixel position 40. Correcting such that the zero-loss peak always matches the reference pixel position 40 in this way makes the peak appear at an accurate position without a spectrum shift shown in FIG. 3(*b*), and makes the measurement highly accurate.

The following section describes a second embodiment of the present invention. FIG. 4(*a*) shows a schematic of a specimen to be measured. The specimen has a structure of laminating a material A (constituting element: A), a material with an unknown constituting element (constituting element is assumed to be B), and material and material C (constituting element C), and a line analysis is applied to the individual materials in a sequence of the material A, the material B, and the material C as shown in FIG. 4(*a*).

An operator simply (1) specifies a start point and an end point of a line to be measured, and (2) participates in a specification process for an element to be analyzed, or an energy range to be measured, and the controller 26 consecutively conducts the operations of (3) energy correction processing for the spectrum, (4) spectrum measuring, and (5) controlling the electron beam position on the specimen until the electron beam reaches the end point specified by the operator. An existence of the energy shift is always detected while measuring a spectrum, and the deviation is detected if the energy of the spectrum shifts, the deviation of the spectrum is converted into a voltage or a current for controlling the drift tube 19, the magnetic field sector 11, or the electron beam source 1 for controlling the spectrum position on the electron beam detector 13 based on the dispersion of the spectrum, thereby correcting the deviation of the spectrum during measuring the spectrum. Measuring the spectrum in this way allows measuring the electron energy loss spectrum at high precision and at high accuracy.

FIG. 4(*b*) shows an example measured by the apparatus of the present embodiment. Peaks respectively appear at energy (a), (b), and (c) on an electron energy loss spectrum when the electron beam exists on the materials A, B, and C as shown in FIG. 4(*b*), and the measuring accuracy of these peak positions is 0.25 eV. Due to the disturbance, it is impossible to measure accurately the electron energy loss spectrum as shown in FIGS. 10*c* and 10*d*.

The following section describes a third embodiment of the present invention. The energy can be corrected even when a zero-loss peak does not appear on the electron beam detector 13 with the apparatus of the present invention. (122) Automatic zero-loss electron retrieval in FIG. 2(*e*) shows the procedure of this process.

An operator simply presses the button to conduct the automatic zero-loss peak retrieval, for example, and the controller 26 (1) detects a position for the largest peak (zero-loss peak). If (1)' the largest peak (zero-loss peak) does not exist on the electron beam detector 13, the drift tube 19 or the magnetic field sector 11 are controlled such that the zero-loss peak appears on the electron beam detector 13, (2) a deviation between the reference pixel position of the electron beam detector 13 and the zero-loss peak position appearing as the result of the operation (1) or (1)', and (3) the drift tube 19 or the magnetic sector 11 are controlled so as to correct the deviation based on the spectrum dispersion. Controlling the controller 26 in this way allows an operator to automatically correct the zero-loss peak position with a single operation. A zero-loss peak is automatically detected, and is moved on the electron beam detector 13, and the energy is corrected when the zero-loss peak does not appear on the electron beam detector 13. The button for conducting the automatic zero-loss peak retrieval is provided as a keyboard or a dedicated button when an operator operates. Pressing this button makes the controller 26 conducts the processing described above.

When the number of pixels of the electron beam detector is 1024 channels, and the dispersion of the electron energy loss spectrum is 0.25 eV per channel, the detectable energy range with the electron beam detector is 256 eV. Because of the limitation on the energy range detected by one electron beam detector once, when a spectrum of electrons which lose energy of 256 eV or more is measured, it is required to correct energy and measure a spectrum alternately using the zero-loss peak with one electron beam detector. When the two electron beam detectors are used, however, one detects the zero-loss peak to correct the energy, and the remaining one measures the electron energy loss spectrum.

One of two electron beam detectors corrects the energy using the zero-loss peak, and the remaining one detects electron beam intensity forming a electron energy loss spectrum at the individual pixels, conducts an operation using electron beam intensities in multiple energy ranges specified before hand, and shows the operation results as image, thereby allowing observing an element distribution image with an energy resolution at high precision. The operation described before includes an operation subtracting a background for a core loss peak part caused by inner shell excited electrons, and dividing electron beam intensity for the core loss peak part by electron beam intensity with energy loss lower than that.

The present invention provides an apparatus and a method for obtaining a high precision electron energy loss spectrum with an electron microscope provided with an electron energy loss spectrum apparatus.

What is claimed is:

1. An element distribution image observing apparatus comprising:

an electron beam source for generating an electron beam;

a lens for converging an electron beam after transmitting through a specimen;

at least two electron beam detectors for detecting an electron beam which has been transmitted through said specimen at an energy dispersion surface, said electron beam detectors further comprising:

a maximum intensity peak position detector for detecting a peak position where an electron beam intensity is at maximum in an electron energy loss spectrum formed by the electron beam which has been transmitted through the specimen, and an electron beam detector for detecting a beam which has lost energy;

a controller for detecting a deviation value between a peak position of electron intensity detected by said maximum intensity peak position detector, and a reference pixel position on said maximum intensity peak position detector, and for correcting the deviation value;

an operation unit for calculating signals from said electron beam detector for detecting a beam which has lost energy; and an image apparatus for showing the element distribution derived from a calculation result from said operation unit.

2. An element distribution image observing apparatus comprising:

an electron beam source for generating an electron beam;

a lens for converging an electron beam after transmitting through a specimen;

an electron beam detector for detecting an electron beam which has been transmitted through said specimen at an energy dispersion surface, said electron beam detector detecting at least a peak position where an electron beam intensity is at maximum in an electron energy loss spectrum formed by the electron beam which has been transmitted through the specimen, and a beam which has lost energy;

a controller for detecting a deviation value between a peak position of electron intensity detected by said maximum intensity peak position detector, and a reference pixel position on said maximum intensity peak position detector, and for correcting the deviation value;

an operation unit for calculating signals from said electron beam detector for detecting a beam which has lost energy; and an image apparatus for showing the element distribution derived from a calculation result from said operation unit.

3. An electron beam energy loss spectrum measuring apparatus comprising:

at least two electron beam detectors including multiple pixels, and for measuring a spectrum of an electron beam transmitted through a specimen at an energy dispersion surface;

an energy filter controller for controlling the position of said electron beam coming into said electron beam detector, an operation unit, and a central controller for controlling said energy filter controller and said operation unit;

a lens for adjusting a focus of an electron beam energy loss spectrum; and a controller for controlling a peak where an electron beam intensity is at a maximum in an electron beam energy loss spectrum, and for controlling such that a full-width of the peak at a half-maximum of the peak is at a minimum and/or a peak intensity is at a maximum;

wherein the position of a peak appearing on a spectrum detected by said at least two electron beam detectors is detected as a peak pixel position of said at least two electron beam detectors, a position deviation value between a reference pixel position designated as a reference position on said at least two electron beam detectors and said peak pixel position is detected, said position deviation value is converted into a control factor for controlling the position of said electron beam, and said position deviation value is corrected based on said control factor.

4. A method for observing distribution image of an element to be measured comprising steps of:

specifying an element to be measured, an energy value to be measured, or an energy range to be measured;

generating an electron beam;

converging an electron beam after transmitting through a specimen;

detecting an electron beam which has been transmitted through said specimen at an energy dispersion surface using at least two electron beam detectors;

detecting a peak where an electron beam intensity of the loss spectrum is at maximum and a deviation value of the peak position where the electron beam intensity is at maximum from a reference position;

correcting the deviation value;

measuring an energy loss spectrum of the specified element or specified energy-range;

calculating a peak of the specified element using an electron beam intensity of the loss energy lower than the specified element;

memorizing and displaying the peak intensity of the specified element obtained by the calculation in response to the electron beam position on the specimen; and measuring an electron energy loss spectrum during controlling the electron beam position.

5. An electron energy loss spectrometer comprising:

at least two electron beam detectors for detecting an electron beam which has been transmitted through a specimen, said at least two electron beam detectors further comprising:

a maximum intensity peak position detector for detecting a peak position where an electron beam intensity is at maximum in an electron energy loss spectrum formed by the electron beam which has been transmitted through the specimen at an energy dispersion surface, and an electron beam detector for detecting a beam which has lost energy;

a controller for detecting a deviation value between a peak position of electron intensity detected by said maximum intensity peak position detector, and a reference pixel position on said maximum intensity peak position detector, and for correcting the deviation value;

an energy-dispersing means for dispersing electron energy; and an energy selection slit for selecting the electron beam dispersed on a dispersion plane of said energy-dispersing means by the energy electron beam in said at least two electron beam detectors, said maximum intensity peak position detector being arranged on the energy dispersion plane;

wherein the controller controls a condition for controlling an electron beam source, a draft tube, or a magnetic field sector so that trajectories of the electrons are corrected and the deviation of the peak position becomes small.

6. An electron beam energy loss spectrum measuring apparatus comprising:

an electron beam detector including multiple pixels, and for measuring a spectrum of an electron beam transmitted through a specimen at an energy dispersion surface;

an energy filter controller for controlling the position of said electron beam coming into said electron beam detector, an operation unit, and a central controller for controlling said energy filter controller and said operation unit;

a lens for adjusting a focus of an electron beam energy loss spectrum; and a controller for controlling a peak where an electron beam intensity is at a maximum in an electron beam energy loss spectrum, and for controlling such that a full-width of the peak at a half-maximum of the peak is at a minimum and/or a peak intensity is at a maximum;

wherein the position of a peak appearing on a spectrum detected by said electron beam detector is detected as a peak pixel position of said electron beam detector, a position deviation value between a reference pixel position designated as a reference position on said electron beam detector and said peak pixel position is detected, said position deviation value is converted into a control factor for controlling the position of said electron beam, and said position deviation value is corrected based on said control factor;

wherein the controller controls a condition for controlling an electron beam source, a draft tube, or a magnetic field sector so that trajectories of the electrons are corrected and the deviation of the peak position becomes small.

7. A method for observing distribution image of an element to be measured comprising steps of:

specifying an element to be measured, an energy value to be measured, or an energy range to be measured;

generating an electron beam;

converging an electron beam after transmitting through a specimen;

detecting an electron beam which has been transmitted through said specimen at an energy dispersion surface using an electron beam detector;

detecting a peak where an electron beam intensity of the loss spectrum is at maximum and a deviation value of the peak position where the electron beam intensity is at maximum from a reference position;

correcting the deviation value;

measuring an energy loss spectrum of the specified element or specified energy range;

calculating a peak of the specified element using an electron beam intensity of the loss energy lower than the specified element;

memorizing and displaying the peak intensity of the specified element obtained by the calculation in response to the electron beam position on the specimen; and measuring an electron energy loss spectrum during controlling the electron beam position.

8. An electron energy loss spectrometer comprising:

electron beam detectors for detecting an electron beam which has been transmitted through a specimen at an energy dispersion surface, said electron beam detector further comprising:

a maximum intensity peak position detector for detecting a peak position where an electron beam intensity is at maximum in an electron energy loss spectrum formed by the electron beam which has been transmitted through the specimen, and an electron beam detector for detecting a beam which has lost energy;

a controller for detecting a deviation value between a peak position of electron intensity detected by said maximum intensity peak position detector, and a reference pixel position on said maximum intensity peak position detector, and for correcting the deviation value;

an energy-dispersing means for dispersing electron energy; and an energy selection slit for selecting the electron beam dispersed on a dispersion plane of said energy-dispersing means by the energy electron beam in said at least two electron beam detectors, said maximum intensity peak position detector being arranged on the energy dispersion plane;

wherein the controller controls a condition for controlling an electron beam source, a draft tube, or a magnetic field sector so that trajectories of the electrons are corrected and the deviation of the peak position becomes small.

* * * * *